United States Patent
Chugunov et al.

(10) Patent No.: US 8,452,539 B2
(45) Date of Patent: *May 28, 2013

(54) METHOD AND APPARATUS UTILIZING NUCLEAR MAGNETIC RESONANCE MEASUREMENTS FOR ESTIMATING RESIDUAL CARBON DIOXIDE SATURATION IN AQUIFIERS

(75) Inventors: Nikita V. Chugunov, Arlington, MA (US); Terizhandur S. Ramakrishnan, Boxborough, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 288 days.

This patent is subject to a terminal disclaimer.

(21) Appl. No.: 12/909,116

(22) Filed: Oct. 21, 2010

(65) Prior Publication Data
US 2012/0101730 A1    Apr. 26, 2012

(51) Int. Cl.
*G01V 3/00* (2006.01)

(52) U.S. Cl.
USPC ............................................. 702/8; 324/303

(58) Field of Classification Search
USPC ...................... 702/8, 11; 324/303, 309; 703/6, 703/10
See application file for complete search history.

(56) References Cited

U.S. PATENT DOCUMENTS

| | | | |
|---|---|---|---|
| 5,363,041 A | 11/1994 | Sezginer | |
| 7,221,158 B1 * | 5/2007 | Ramakrishnan | 324/303 |
| 2010/0299126 A1 * | 11/2010 | Chugunov et al. | 703/10 |

OTHER PUBLICATIONS

Frisch et al., "Percolation Process and Related Topics," Journal of the Society for Industrial and Applied Mathematics, Dec. 1963, vol. 11(4): pp. 894-918.
Timur, A., "Pulsed Nuclear Magnetic Resonance Studies of Porosity, Moveable Fluid, and Permeability of Sandstone," Journal of Petroleum Technology, Jun. 1969, vol. 21: pp. 775-786.
Shante et al., "An Introduction to Percolation Theory," Advances in Physics, 1971, vol. 20(80): pp. 325-357.
Essam, "Percolation Theory," Reports on Progress in Physics, Jul. 1980, vol. 43(7): pp. 833-912.
Mohanty, "Fluids in Porous Media: Two-Phase Distribution and Flow," Ph.D. thesis, University of Minnesota, 1981: pp. A15-A17, D1-D7, D101-D104 and E1-E10.
Ramakrishnan, T. S., and Wasan, D. T., "Two-Phase Distribution in Porous Media: An Application of Percolation Theory," International Journal of Multiphase Flow, 1986, vol. 12(3): pp. 357-388.
Kenyon et al., "A Three-Part Study of NMR Longitudinal Relaxation Properties of Water-Saturated Sandstones," SPE Formation Evaluation, Sep. 1988, vol. 3(3): pp. 622-636.
Kenyon et al., "Erratum," SPE Formation Evaluation, 1989, vol. 4(1): p. 8.
Hurlimann et al., "Restricted Diffusion in Sedimentary Rocks: Determination of Surface-Area to Volume Ratio and Surface Relaxivity," Journal of Magnetic Resonance, Series A., Dec. 1994, vol. 111(2): pp. 169-178.

(Continued)

*Primary Examiner* — Bryan Bui
(74) *Attorney, Agent, or Firm* — Rachel E. Greene; Jakub Michna; Bridget Laffey

(57) ABSTRACT

Percolation theory is applied to establish a connection between magnetization decay of nuclear magnetic resonance (NMR) measurements and residual carbon dioxide saturation ($S_{cr}$). As a result, estimations of $S_{cr}$ are obtained through use of an NMR tool in a formation and appropriate processing. Data may be displayed as a log.

20 Claims, 6 Drawing Sheets

OTHER PUBLICATIONS

Helton et al., "Latin Hypercube Sampling and the Propagation of Uncertainty in Analyses of Complex Systems," Reliability Engineering and System Safety, 2003, vol. 81: pp. 23-69.

Arns et al., "Prediction of Permeability from NMR Response: Surface Relaxivity Heterogeneity," SPWLA 47th Annual Logging Symposium, Jun. 2006: pp. 1-13.

* cited by examiner

METHOD AND APPARATUS UTILIZING NUCLEAR MAGNETIC RESONANCE MEASUREMENTS FOR ESTIMATING RESIDUAL CARBON DIOXIDE SATURATION IN AQUIFERS

BACKGROUND OF THE INVENTION

1. Field of the Invention

This invention relates broadly to estimating residual carbon dioxide ($CO_2$) saturation in aquifers. More particularly, this invention relates to estimating residual $CO_2$ saturation ($S_{cr}$) from nuclear magnetic resonance (NMR) measurements obtained by a logging tool.

2. State of the Art

Elevated carbon dioxide concentration in the atmosphere is widely accepted as a contributor to global climate change. Carbon capture and sequestration (CCS) is one of the pursued technologies to reduce atmospheric accumulation of $CO_2$.

Suitability of a carbon dioxide geological storage site is commonly characterized by three metrics: capacity, injectivity, and containment. Evaluation of these three performance measures at early stages of a $CO_2$ storage project relies largely upon seismic and well characterization, reservoir modeling, and simulation. Petrophysical properties such as porosity, permeability, and residual saturation of aqueous and $CO_2$-rich phases describe the target formation zone, and serve as inputs for simulation models. The estimates for these properties are usually inferred from wireline measurements. Porosity is usually estimated based on neutron scattering and density measurements, while permeability is commonly inferred from NMR measurements. See, Timur, A. "Pulsed Nuclear Magnetic Resonance Studies of Porosity, Movable Fluid, and Permeability of Sandstones, *Journal of Petroleum Technology*, 21:775-786 (1969); Kenyon, W. E., et al., "A Three-part Study of NMR Longitudinal Relaxation Properties of Water-Saturated Sandstones, *SPE Formation Evaluation*, 3:622-636 (1988); Kenyon, W. E., et al., "Erratum", *SPE Formation Evaluation*, 4:8 (1989). In practice, NMR based inference is not absolute and requires zonal calibration. Methods for evaluating surface relaxivity from stationary formation tests to calibrate NMR logs are proposed in U.S. Pat. No. 7,221,158 to Ramakrishnan which is hereby incorporated by reference herein in its entirety.

In geological storage, brine displaced by $CO_2$ counter-imbibes to form trapped or residual $CO_2$. This refers to the part of the $CO_2$-rich phase disconnected from the rest of the phase exhibiting pressure continuity. Unlike oil wells, in geological storage sites, $CO_2$ is not present during drilling. Therefore drilling fluid filtrate invasion consists of a single phase displacement, and an estimate of $S_{cr}$ cannot be obtained. While estimations of residual saturations can be obtained as part of an advanced core analysis which is conducted in the lab through displacement experiments, laboratory methods are laborious and are available only at formation locations and depths which have been subjected to coring. As will be appreciated by those skilled in the art, formation coring is slow and expensive, and provides information for only the specific coring locations. Given the desire to rapidly develop geological $CO_2$ storage worldwide, reliance on coring is not a suitable option.

SUMMARY OF THE INVENTION

In accord with the present invention, residual carbon dioxide saturation is estimated from NMR measurements obtained by a logging tool.

According to one aspect of the invention, utilizing NMR measurements, residual carbon dioxide saturations $S_{cr}$ are estimated as a function of depth in a borehole, and a continuous log may be presented.

According to one embodiment, the porous medium of the formation is approximated by a parameterized pore-level percolation model. The values of the model parameters are inferred from petrophysical measurements that also relate to the same parameters, or are estimated for known types of formations. The remaining petrophysical properties of the modeled medium, e.g. residual $CO_2$ saturation, are then calculated from the pore level model. Thus, it is expected that the inferences and the measurements of reservoir properties will be self-consistent within the percolation framework. More particularly, percolation theory is applied to establish a connection between magnetization decay of NMR measurements and residual $CO_2$ saturation, and algorithms are provided for calculating $S_{cr}$ based on available petrophysical data.

In one embodiment, $S_{cr}$ is estimated from NMR measurements in the absence of other data. In another embodiment $S_{cr}$ is estimated from NMR measurements in view of independent residual water saturation ($S_{wr}$) determinations. In yet another embodiment, $S_{cr}$ is estimated from NMR measurements in view of independent permeability measurements. In all three embodiments, continuous logs of $S_{cr}$ may be generated.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
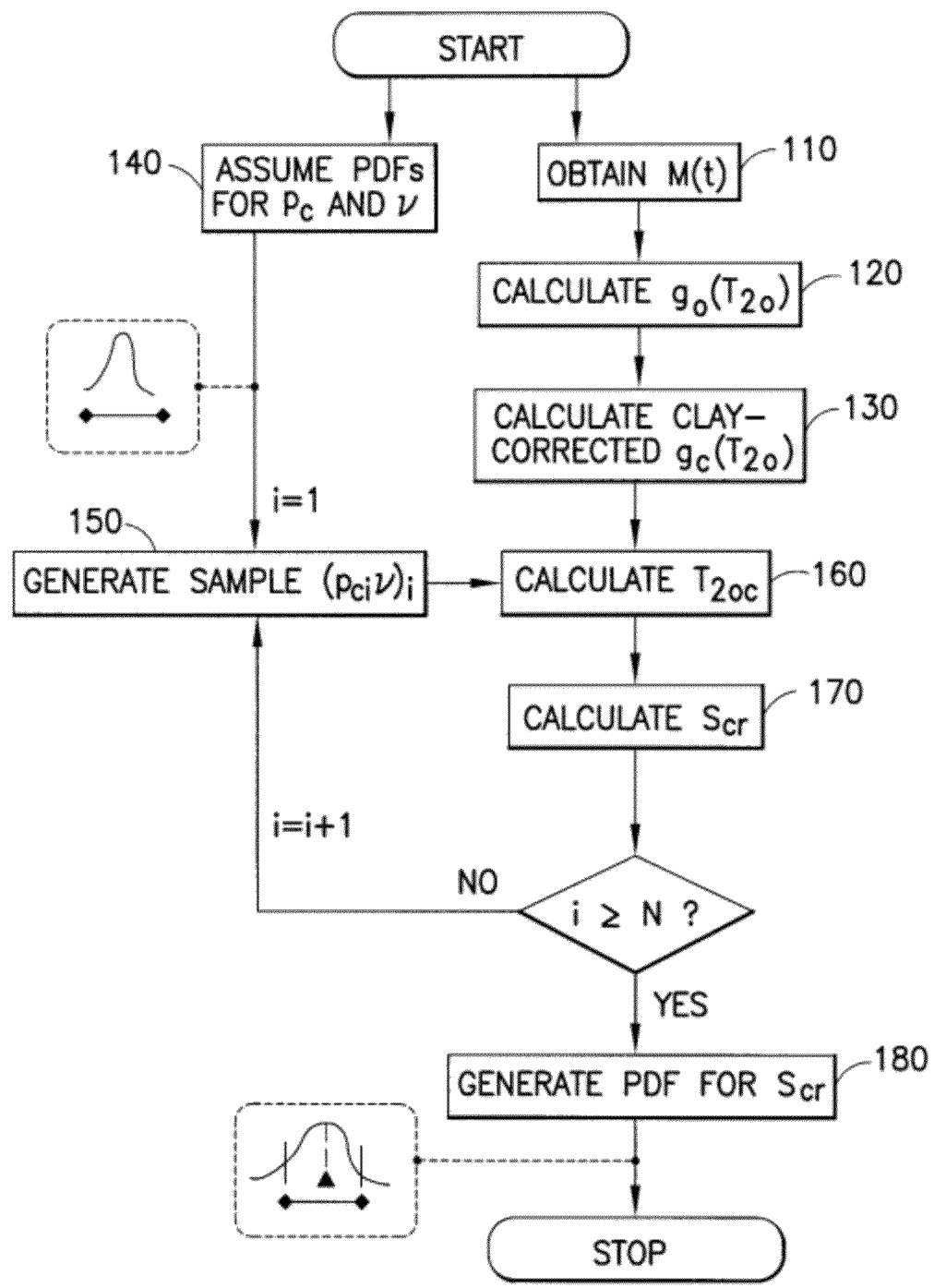
FIG. 1 is a flow chart of a first embodiment of a method for generating residual carbon dioxide saturation estimations as a function of depth.

Prior to turning to the drawings, an understanding of the theoretical underpinnings of the methods of the invention is desirable.

The theoretical basis for the methodology of the invention is a percolation network model. Based on assumptions (e.g. a water-wet medium, a one-to-one size correspondence between pore throats and pore body), the pore size NMR relaxation distribution may be related to permeability and residual saturations of both the wetting and non-wetting phases using percolation theory. The first step to carry this out is to relate the observed magnetization relaxation to a transverse relaxation time distribution.

As in previously incorporated U.S. Pat. No. 7,221,158, the transverse magnetization decay from NMR measurements is denoted as M(t), and it is assumed that the formation pore space can be represented by a probability density function of pore sizes, with relaxation in each pore being surface relaxivity controlled. Assuming a sufficiently short echo spacing in the NMR measurements (e.g., CPMG echo spacing used in current NMR tools such as the CMR tool of Schlumberger is 0.2 ms), the diffusion in the observed spin-spin relaxation may be ignored. Thus, the observed relaxation time ($T_{2o}$) associated with each pore is defined according to $$\frac{1}{T_{2o}} = \frac{1}{T_{2b}} + \frac{\rho}{l}, \qquad (1)$$

where $T_{2b}$ is the bulk transverse relaxation time of the fluid (for water, $T_{2b}$ is in the range of 2.5-3 s), l is the volume to surface area ratio of the pore, and $\rho$ is surface relaxivity. If $g_l(l)$ is the volume probability density function of l, then, by definition, $$\int_0^\infty g_l(l)dl = 1. \qquad (2)$$

Combining Eq. 1 and Eq. 2, the spin-spin relaxation probability density function with respect to $T_{2o}$ is defined by $$\int_0^{T_{2b}} g_o(T_{2o})dT_{2o} = 1, \qquad (3)$$

where $$T_{2o} = \frac{l}{l + \rho T_{2b}} T_{2b}; \qquad (4)$$

$$g_o(T_{2o}) = \frac{1}{\rho}\left(\frac{l}{T_{2o}}\right)^2 g_l(l)$$

Since the transverse magnetization relaxation in each pore decays as $\exp(-t/T_{2o})$, the total observed magnetization measured by an NMR tool represents volumetric superposition of responses from all pores according to:

$$M(t) = \phi \int_0^{T_{2b}} g_o(T_{2o}) \exp(-t/T_{2o}) dT_{2o}. \qquad (5)$$

U.S. Pat. No. 5,363,041 to Sezginer which is hereby incorporated by reference herein in its entirety discloses a computational procedure to determine $g_o(T_{2o})$ from M(t) using singular value decomposition.

Among the properties governing transport equations in porous media, residual saturations of the wetting and non-wetting phases are of particular interest. According to Ramakrishnan, T. S. and Wasan, D. T., "Two-phase Distribution in Porous Media: An Application of Percolation Theory", *Int. J. Multiphase Flow*, 12(3):357-388 (1986), the residual wetting phase is trapped in small pores that are not accessed from the boundary by a connected path of pore filled wetting phase. The residual wetting phase may however be connected to the boundary through thin films or through roughness filling fluid. The wetting phase trapping may be characterized by the cumulative relaxation response from the portion of pores up to certain critical characteristic pore-size $l_{wc}$. In terms of spin-spin relaxation time, the residual wetting phase saturation $S_{wr}$ can be determined from $$S_{wr} = \int_0^{T_{2wc}} g_o(T_{2o})dT_{2o}, \qquad (6)$$

where $T_{2wc}$ is the critical spin-spin relaxation time related to the pore-size characterized by $l_{wc}$ via Eq. 1. The critical $l_{wc}$ is quantified below.

Unlike the wetting phase, the non-wetting phase is trapped when disconnected from the rest of the flowing phase and has no thin film interconnections. The isolated blobs are separated or surrounded by the wetting phase. As suggested by Mohanty, K. K., "Fluids in Porous Media: Two-Phase Distribution and Flow, Ph.D. Thesis, University of Minnesota (1981) and Ramakrishnan, T. S. and Wasan, D. T., "Two-phase Distribution in Porous Media: An Application of Percolation Theory", *Int. J. Multiphase Flow*, 12(3):357-388 (1986), two different entrapment mechanisms exist. The first one is a snap-off event and is caused by the instability of the wetting phase thin film when the pore body to pore throat size ratio is large. The second mechanism called by-pass occurs when finite clusters of the non-wetting phase are formed by the advancing wetting phase due to multiple connections existing in the pore space that allow occupancy of the surrounding pores before displacing the cluster filling non-wetting fluid. Thus, trapping of the non-wetting phase occurs when a set of large pores is wholly surrounded by smaller pores. During imbibition, the wetting fluid will advance by occupying the pore-space from lower to higher pores sizes, but constrained by connectivity of both advancing and receding phases. When the occupancy for the advancing wetting phase allows a critical length scale $l_c$, the non-wetting phase becomes disconnected, and no further removal is possible. In fact, the above-mentioned critical length scale $l_c$ will represent the most resistant connection in the least resistant pathway, and is given by the smallest pore size within the set of largest pore sizes that form a sample spanning pathway as set forth in previously incorporated U.S. Pat. No. 7,221,158 to Ramakrishnan. This is discussed in more details below.

Transforming critical length scale $l_c$ into critical relaxation time $T_{2oc}$ via Eq. 1, an estimate is obtained for the lower bound of the residual non-wetting phase saturation $S_{cr}$:

$$S_{cr} \approx \int_{T_{2oc}}^{T_{2b}} g_o(T_{2o})dT_{2o}. \qquad (7)$$

This is a lower bound because it accounts only for the non-wetting phase that occupies pores with $l > l_c$. In reality, the isolated clusters may contain pores smaller than $l_c$. The above equation neglects some of the trapping that occurs before the wetting phase is allowed to occupy $l_c$. Therefore, Eq. 7 is to be regarded as an approximation for $S_{cr}$, and is satisfactory for lattices with large coordination numbers. See, Ramakrishnan, T. S. and Wasan, D. T., "Two-phase Distribution in Porous Media: An Application of Percolation Theory", *Int. J. Multiphase Flow*, 12(3):357-388 (1986).

As will be now appreciated, percolation theory may be used to interpret NMR measurements. First, the relationship between the number probability density function $n_l(l)$ and $g_l(l)$ may be written as $$n_l(l) = \frac{g_l(l)/V(l)}{\int_0^\infty g_l(l)/V(l)dl}, \qquad (8)$$

assuming that the volume of the pore V is determined by the single length scale l. A pore shape parameter v can be introduced to quantify this relationship as $$V(l) \propto l^v. \qquad (9)$$

This relation and values of v for sinusoidal and rectangular pores are investigated in Ramakrishnan, T. S. and Wasan, D. T., "Two-phase Distribution in Porous Media: An Application of Percolation Theory", *Int. J. Multiphase Flow*, 12(3):357-388 (1986). In addition, previously incorporated U.S. Pat. No. 7,221,158 states that the value of v may vary from 0 to 3, depending on the pore shape. For example, for spherical pores, v=3, neglecting the volume contained in the pore throats.

The proposed approximation of the in situ formation is based on the site percolation model, where the pore space is represented by the lattice of sites connected by bonds. See, Essam, J. M. "Percolation Theory", *Rep. Prog. Phys.*, 43:834-912 (1980) and Shante, V. K. S., and Kirkpatrick, S., "An Introduction to Percolation Theory", *Adv. Phys.*, 20:325-357 (1971). The sites are made accessible for the fluid with a fixed probability p, and the fluid cannot advance through a blocked site. The transport property of the percolation model is then characterized by the critical percolation probability $p_c$, defining the maximum p, below which the probability of creating the connected path between the opposite sides of the lattice is zero, Frish, H. L., and Hammersley, J. M., "Percolation Processes and Related Topics", *J. Soc. Induct. Math.*, 11:894-918 (1963), i.e., the non-wetting phase is still immobile.

In terms of number probability function (see Eq. 8) and the critical length scale $l_c$, the critical percolation probability $p_c$ can be expressed as $$p_c = \int_{l_c}^{\infty} n_f(l) dl. \quad (10)$$

Substituting $n_f(l)$ from Eq. 8 in Eq. 10 with the assumption from Eq. 9 and making variable transformation from l to $T_{2o}$ using Eq. 1, an expression is obtained for the critical percolation probability via $T_{2oc}$, spin-spin relaxation distribution $g_o(T_{2o})$, and pore geometry factor v:

$$p_c = \frac{\int_{T_{2oc}}^{T_{2b}} T_{2o}^{-\nu}(T_{2b} - T_{2o})^\nu g_o(T_{2o}) dT_{2o}}{\int_{T_0}^{T_{2b}} T_{2o}^{-\nu}(T_{2b} - T_{2o})^\nu g_o(T_{2o}) dT_{2o}}. \quad (11)$$

Similarly, if the percolation approach is applied to understand residual water saturation, it will be appreciated that the largest pore size $l_{wc}$ from the set of smallest pores constituting the fraction equal to critical percolation probability $p_c$ is of interest. Thus, Eq. 10 transforms to $$p_c = \int_0^{l_{wc}} n_f(l) dl \quad (12)$$

Thus, Eq. 11 for wetting phase percolation model will be $$p_c = \frac{\int_0^{T_{2wc}} T_{2o}^{-\nu}(T_{2b} - T_{2o})^\nu g_o(T_{2o}) dT_{2o}}{\int_0^{T_{2b}} T_{2o}^{-\nu}(T_{2b} - T_{2o})^\nu g_o(T_{2o}) dT_{2o}} \quad (13)$$

where $T_{2wc}$ is a critical observed spin-spin relaxation time corresponding to the critical length scale $l_{wc}$ (also see Eq. 6).

According to one embodiment of the invention, the spin-spin relaxation distribution $g_o(T_{2o})$ should account for the presence of clay. Clay tends to form a micro-porous coating at the surface of the pore or it may occur in clumps essentially not participating in the fluid flow. The common structure of this coating can be represented by a stack of platelets. Water is effectively trapped in the clay and cannot be displaced by another fluid under normal circumstances of displacement. Presence of clay in the pore structure affects the interpretation of NMR. In other words, given a volume density function, the number density function is highly skewed towards small pores. These small pores do not participate in percolation-like displacement and should therefore be discounted. One may perceive of them to add to the inventory of the wetting phase without affecting displacement processes.

Since pores classified as clays have a distinctly small size compared to the rest of the porous medium, a cut-off relaxation time $T_2$ below which only pores constituting clay are present is expected. This cut-off time labeled $T_{2cb}$ corresponds to the largest pores within the clay and they do not see a phase replacement. It is therefore appropriate to compute "clay-bound" water from $$S_{wb} = \int_0^{T_{2cb}} g_o(T_{2o}) dT_{2o} \quad (14)$$

where the commonly used value for $T_{2cb}$ is 3 ms.

The clay contribution to the observed relaxation $g_o(T_{2o})$ is excluded from pore size distribution used to build the percolation model. Therefore, according to the embodiment, the clay-corrected relaxation distribution $g_c(T_{2o})$ accounting for the presence of clay should be used in Eq. 11 and Eq. 13 in lieu of $g_o(T_{2o})$ $$g_c(T_{2o}) = \begin{cases} 0, & T_{2o} \leq T_{2cb} \\ g_o(T_{2o}) / \int_{T_{2cb}}^{T_{2b}} g_o(T_{2o}) dT_{2o}, & T_{2o} > T_{2cb}. \end{cases} \quad (15)$$

Accounting for the presence of clay does not require revision of Eq. 7 for residual $CO_2$ saturation since $CO_2$ will be trapped in the pores corresponding to relaxation times $T_{2o} > T_{2cb}$, and $S_{cr}$ is calculated as a ratio of the pore-space within which trapping has occurred to the total porosity of the formation. The estimate for residual water saturation $S_{wr}$ (Eq. 6) also holds, since both clay-bound water and residually trapped water contribute to $S_{wr}$. Thus, it is only for the calculation of $T_{2oc}$ and $T_{2wc}$ that $g_c(T_{2o})$ from Eq. 15 is used in the embodiment which accounts for the presence of clay.

Using the theoretical analysis set forth above, the formation may be characterized utilizing NMR data obtained from a borehole tool such as the Combinable Magnetic Resonance tool (CMR—a trademark of Schlumberger), and the MR Scanner tool—a trademark of Schlumberger. The specific method of finding the residual carbon dioxide saturation depends upon the available information which can be used to calibrate the percolation model as described hereinafter. In addition, as will be set forth hereinafter, even in the absence of other petrophysical data, a realistic range for the $S_{cr}$ values may be obtained, and this range can be reduced to a single best estimate if more data to calibrate the underlying percolation model become available. Furthermore, the methods described herein allow consistent propagation of uncertainty in the parameters of the model to characterize uncertainty in the resultant estimation for $S_{cr}$.

Turning to FIG. 1 a first embodiment of a method for estimating residual carbon dioxide values is provided. The first embodiment relates to a situation where only magnetization relaxation data is available. Using an NMR tool (as described in more detail hereinafter with reference to FIG. 4) such as the Schlumberger CMR or CMR-plus tool, for every depth of interest, the transverse magnetization relaxation over time M(t) is measured at 110. Then, utilizing computational procedures such as disclosed in U.S. Pat. No. 5,363,041, the relaxation distribution $g_o(T_{2o})$ is calculated at 120. At 130, the relaxation distribution is optionally corrected for clay content according to Eq. 15. In order to calculate $T_{2oc}$ from the (clay corrected) relaxation distribution, values for critical percolation probability $p_c$ and the pore geometric factor v are required. In the absence of other relevant data, a range for the values of critical percolation probability $p_c$ is assumed to be between 0.2 and 0.3, while that for the pore geometric factor v is assumed to be between 0 and 3. However, if additional data on pore shapes can be inferred from other sources (e.g. core data using CT scans), the default range of values for v may be narrowed. Regardless, the uncertainty in available knowledge about $p_c$ and v may be represented via a probability distribution function (e.g. a normal, log normal, triangular, uniform or other such probability density function) at 140, and random sampling can be used to generate an $i^{th}$ pair of values taken at 150. It will be appreciated that Latin Hypercube Sampling (Helton, J. C. and Davis, F. J., "Latin Hypercube Sampling and the Propagation of Uncertainty in Analyses of Complex Systems", *Reliab Eng Syst Saf*, 81:23-69 (2003)) may provide an efficient manner if generating equiprobable samples from a set of variables defined by their probability distributions. The pair of values is then used in conjunction with the calculated (clay corrected) relaxation distribution to calculate $T_{2oc}$ according to Eq. 11 (optionally in light of Eq. 15). From the calculated $T_{2oc}$, the residual carbon dioxide saturation $S_{cr}$ can be estimated at 170 utilizing Eq. 7.

Figure 5A:
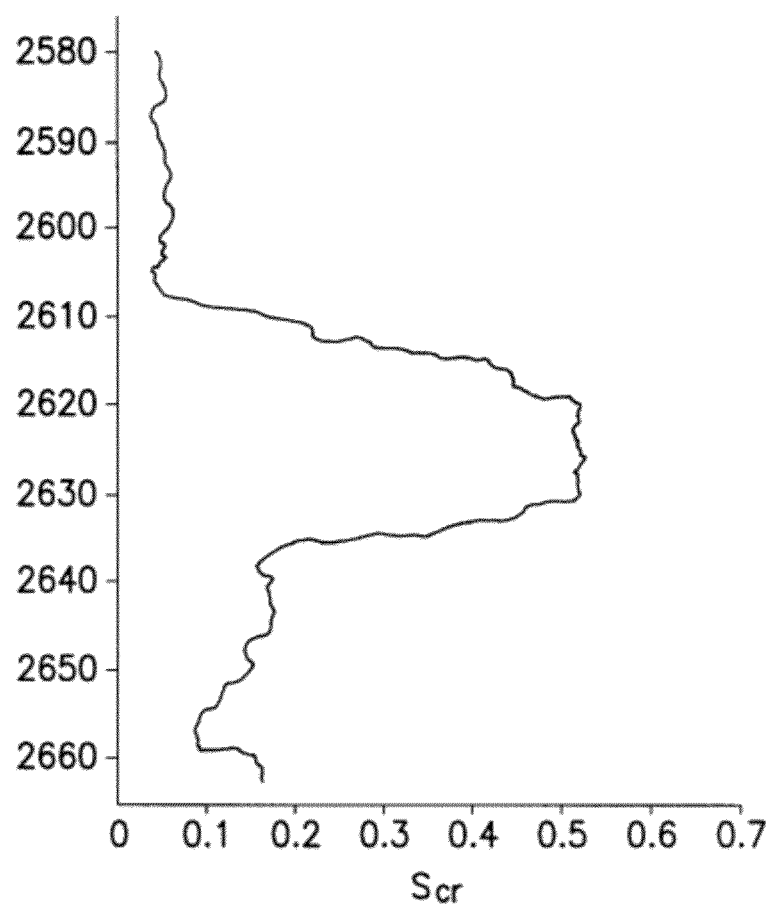
FIG. 5a is a log showing residual carbon dioxide saturation as a function of formation depth.
Figure 5B:
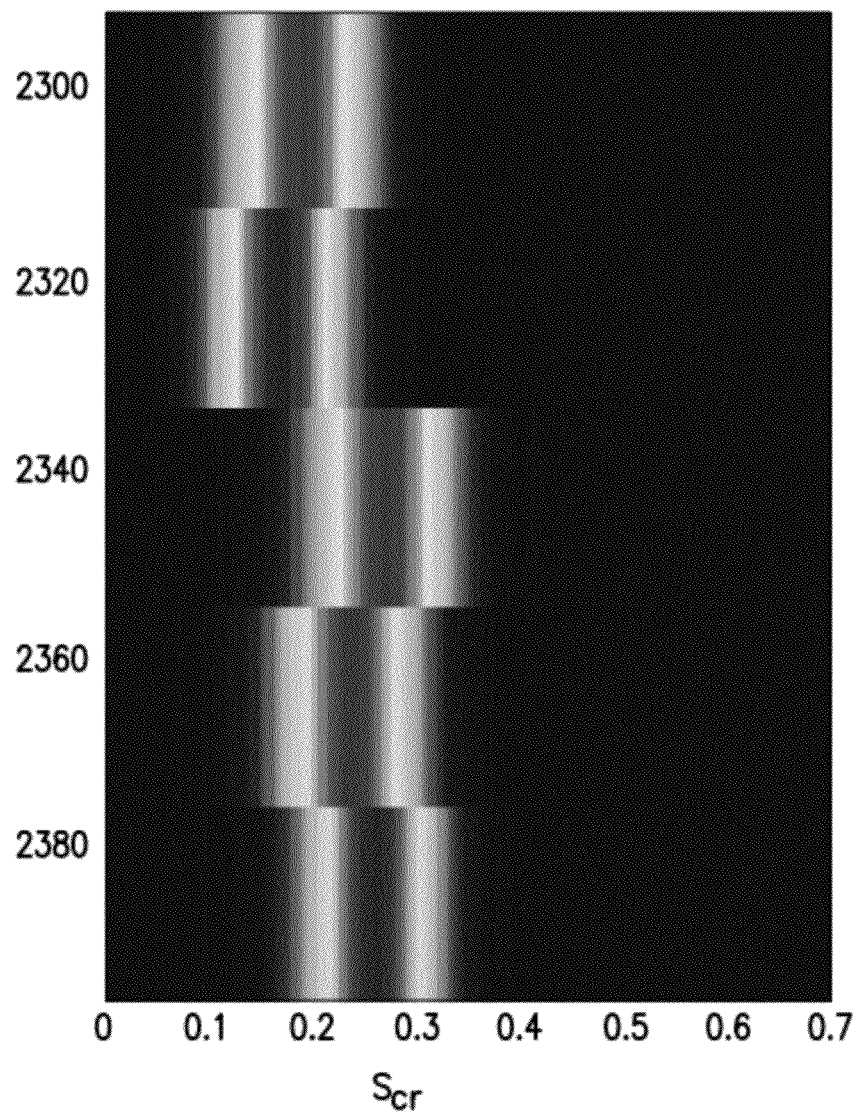
FIG. 5b is a log showing a representation of a probability density function of residual carbon dioxide saturation as a function of formation depth.

As indicated in FIG. 1, because a single pair of values $p_c$ and v were chosen at 150 to be used in calculating $T_{2oc}$ at 160, it is desirable to repeat steps 150-170 a plurality (e.g. N >100) times. Each time, a new pair of values for $p_c$ and v are randomly generated, and used to calculate $T_{2oc}$ and $S_{cr}$. As a result, a probability density function (pdf) of the residual carbon dioxide saturation can be generated for each depth at which NMR data was collected. Alternatively, or in addition, a single best estimate can be calculated as the mean or mode value of the obtained $S_{cr}$ distribution. The results can be generated as a simple log of most likely values as a function of depth (as seen in FIG. 5a described below), or as a log of pdf values as a function of depth using intensity or color (as seen in FIG. 5b described below).

It is noted that if a range of values is specified for $p_c$ and v, only two iterations are needed to calculate a range of possible values for $S_{cr}$, since $S_{cr}$ monotonously increases with increasing v and increasing $p_c$. Therefore, steps 160 and 170 can be performed only for two pairs of percolation parameters: (min ($p_c$); min (v)) and (max ($p_c$); max (v)), thus generating the bounds for $S_{cr}$ for any given depth.

Figure 2:
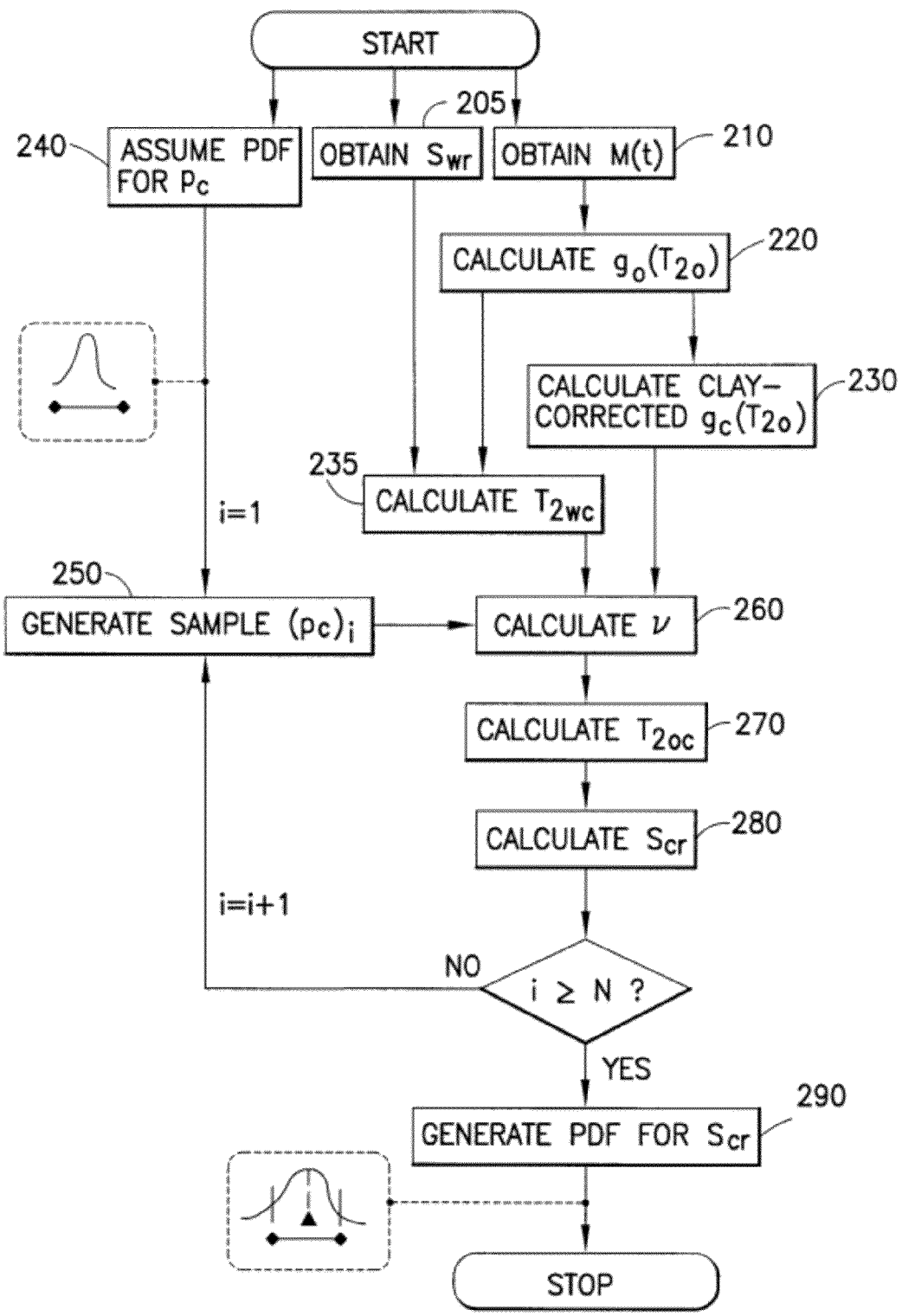
FIG. 2 is a flow chart of a second embodiment of a method for generating residual carbon dioxide saturation estimations as a function of depth.

Turning to FIG. 2, another embodiment of a method for estimating residual carbon dioxide values is provided. This embodiment relates to a situation where residual water saturation ($S_{wr}$) information is obtained at 205 in addition to magnetization relaxation data obtained at 210. It will be appreciated that the residual water saturation may be obtained at 205 from any of several mechanisms including but not limited to core analysis, or scanning using a nuclear logging tool during injection of carbon dioxide into the formation. Regardless, steps 210-230 are identical to steps 110-130 of FIG. 1 where the magnetization relaxation data M(t) obtained from an NMR measurement are transformed into a relaxation distribution (or normalized into a probability density function) $g_o(T_{2o})$ and corrected for the presence of clay. Given the estimate for $S_{wr}$ at 235, Eq. 6 is solved for $T_{2wc}$.

If an estimate for $S_{wr}$ is available at 205, only one of the two parameters of the percolation model has to be "guessed" as the other one can be calculated. Since $p_c$ has a narrower range of possible values compared to that of v, and dependence of $S_{cr}$ on $p_c$ in this range is almost linear, in one embodiment $p_c$ is selected as the parameter to be guessed or assigned a range of possible values (although in another embodiment it will be appreciated that v may be selected as the parameter to be guessed or assigned a range of possible values). At 240, the uncertainty in the estimate of $p_c$ can be represented by probability distribution. N equiprobable values of $p_c$ can then be randomly generated at step 250 using Latin Hypercube Sampling or any other method of random sampling honoring the probability distribution. Then, utilizing values for $T_{2wc}$ and $p_c$, the pore geometry factor v can be calculated at step 260 utilizing Eq. 13, and from the pore geometry factor and the previously calculated (clay-corrected) relaxation distribution (and the same realization for $p_c$ generated at step 250), $T_{2oc}$ is calculated at step 270 according to Eq. 11 (optionally in light of Eq. 15). From the calculated $T_{2oc}$ and the spin-spin relaxation time distribution $g_o(T_{2o})$, the residual carbon dioxide saturation $S_{cr}$ can be estimated at 280 utilizing Eq. 7.

As in the method of FIG. 1 where steps 150-170 were repeated a plurality of times, in the method of FIG. 2, steps 250-290 are performed a plurality (N) times, and at the end of the N-th iteration, N values of $S_{cr}$ are generated. The probability distribution for values of $S_{cr}$ can be calculated at step 290 and presented as a log. In other words, a probability density function (pdf) of the residual carbon dioxide saturation can be generated for each depth at which NMR data was collected. Alternatively, or in addition, a single best estimate can be calculated as the mean or mode value of the obtained $S_{cr}$ distribution. The results can be generated as a simple log of most likely values as a function of depth (as seen in FIG. 5a described below), or as a log of pdf values as a function of depth using intensity or color (as seen in FIG. 5b described below).

According to another embodiment of the invention, if a single value for $S_{wr}$ is not available, but it is possible to obtain a range of $S_{wr}$ from the available petrophysical data or estimate a probability distribution on this range, in lieu of step 205, step 250 can be modified to generate equiprobable realizations of pairs $(p_c; S_{wr})_i$. Then, step 235 will be performed at every $i^{th}$ iteration and precede step 260.

If only maximum and minimum values are specified for $p_c$ at step 240, only two iterations are needed to calculate a range of possible values for $S_{cr}$, since $S_{cr}$ monotonously increases with increasing $p_c$. If only minimum and maximum estimates for $S_{wr}$ are available, the range of possible values of $S_{cr}$ could be estimated based on two iterations for pairs (min ($p_c$), max ($S_{wr}$)) and (max ($p_c$), min ($S_{wr}$)).

Figure 3:
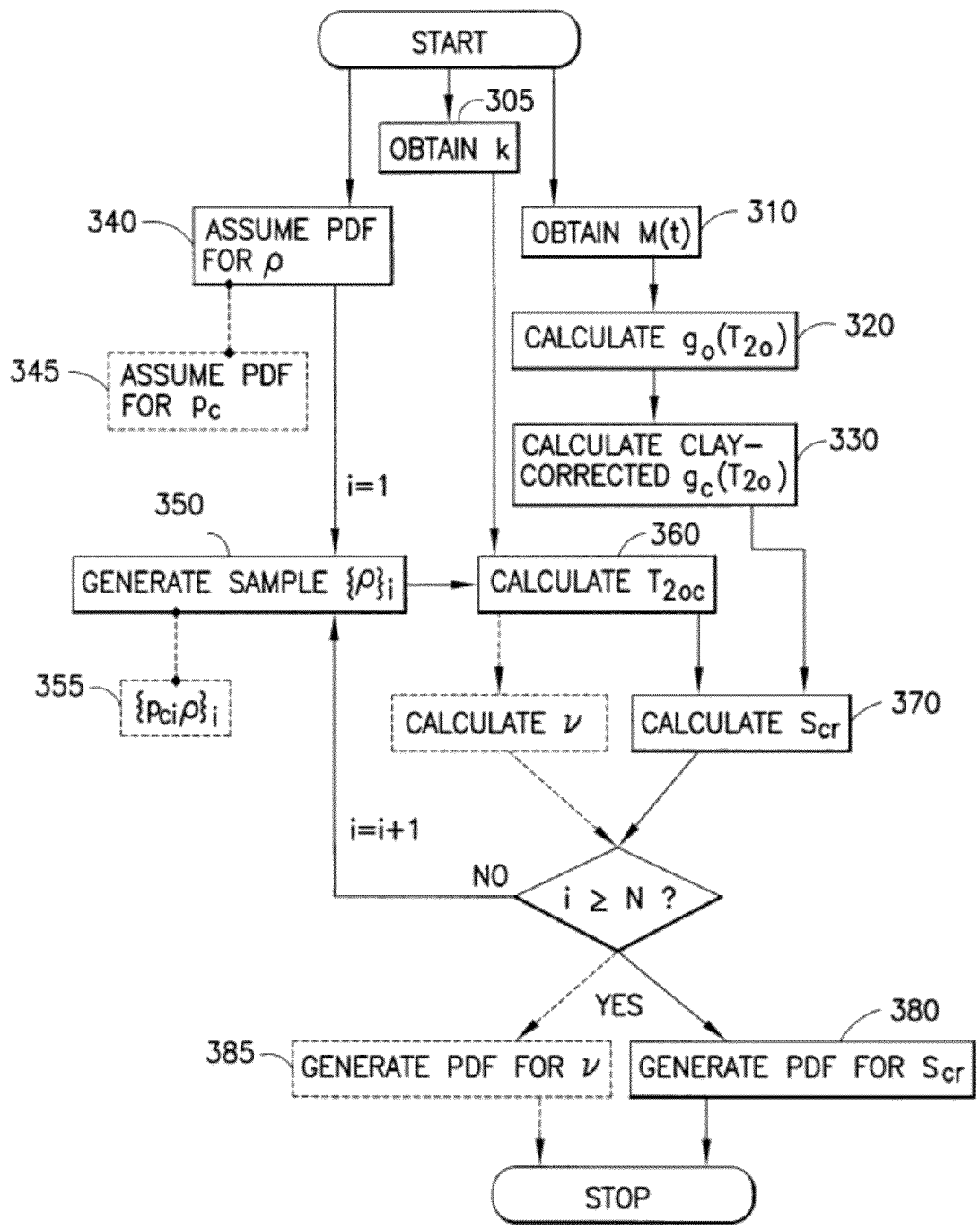
FIG. 3 is a flow chart of a third embodiment of a method for generating residual carbon dioxide saturation estimations as a function of depth.

Turning to FIG. 3, yet another embodiment of a method for estimating residual carbon dioxide values is provided. This embodiment relates to a situation where a permeability estimate k is obtained at 305 in addition to magnetization relaxation data obtained at 310. The permeability estimate may be obtained utilizing injection or drawdown measurements from a formation tester such as the MDT (a trademark of Schlumberger) or in any other desired manner and is used to calculate $T_{2oc}$ as discussed below. In FIG. 3, steps 310, 320, and 330 are the same as steps 110-130 and 210-230 discussed above with reference to FIGS. 1 and 2 and translate M(t) to obtain $g_o(T_{2o})$ and $g_o(T_{2o})$ corrected for the presence of clay.

It will be appreciated that based on percolation theory, and as set forth in previously incorporated U.S. Pat. No. 7,221, 158 to Ramakrishnan, in situ formation permeability is related to the critical relaxation time $T_{2oc}$ according to:

$$k = \frac{\phi^m}{8} \rho^2 \frac{T_{2oc}^2 T_{2b}^2}{(T_{2b} - T_{2oc})^2} \quad (16)$$

where $\phi$ is the porosity (preferably obtained from nuclear or density measurements corrected by an elemental spectroscopy tool as known in the art), m is a constant, and $\rho$ is the surface relaxivity. In order to solve Eq. 16, the value of surface relaxivity $\rho$ is required. It is known that possible values of $\rho$ for sandstone formations can be as low as 4-8 µm/s in Fontainebleau sandstones and as high as 20-26 μm/s in Berea sandstones. In the absence of information about the type of the sandstone formation in hand, one recommended value for ρ is 16 μm/s. Regardless, a probability density function for ρ is generated at 340 from which samples can be generated at 350. Given the values for permeability k, the surface relaxivity ρ, and the bulk fluid relaxation time $T_{2b}$, Eq. 16 can be solved at step 360 for $T_{2oc}$ (with m=2) according to:

$$T_{2oc} = \frac{2\sqrt{2k}}{\phi\rho T_{2b} + 2\sqrt{2k}} T_{2b} \quad (17)$$

From the calculated $T_{2oc}$, the residual carbon dioxide saturation $S_{cr}$ can be estimated at 370 utilizing Eq. 7.

As in the method of FIG. 1 where steps 150-170 were repeated a plurality of times, in the method of FIG. 3, steps 350-380 are performed a plurality (N) times, and at the end of the $N^{th}$ iteration, N values of $S_{cr}$ are generated. The probability distribution for values of $S_{cr}$ can be calculated at step 380 and presented as a log. In other words, a probability density function (pdf) of the residual carbon dioxide saturation can be generated for each depth at which NMR data was collected. Alternatively, or in addition, a single best estimate can be calculated as the mean or mode value of the obtained $S_{cr}$ distribution. The results can be generated as a simple log of most likely values as a function of depth (as seen in FIG. 5a described below), or as a log of pdf values as a function of depth using intensity or color (as seen in FIG. 5b described below).

It should be appreciated that for values of $T_{2b}$=3 s, $\phi$=0.2, and k=100 mD, Eq. 17 results in a value of $T_{2oc}$=0.256 s for ρ=16 μm/s, while the range of ρ from 8 μm/s to 24 μm/s, would produce values for $T_{2oc}$ from 0.471 s to 0.175 s respectively. With increasing $T_{2oc}$ the estimate for $S_{cr}$ decreases (see Eq. 7). The actual amount of decrease will depend on $g_o(T_{2o})$.

The estimated value for $T_{2oc}$ obtained at step 360 can be also used to infer a value for the pore geometry factor v. Since the value of v is not expected to change significantly within the same stratigraphic layer, a single measurement of the permeability k in this layer can provide enough information to calibrate the percolation model for an estimation of $S_{cr}$ based on NMR measurements throughout the layer. More particularly, certain steps of FIG. 3 should be expanded to allow for an estimation of v. Specifically, step 340 could be expanded to include step 345 that provides a probability distribution for the critical percolation probability $p_c$ value. Thus, step 350 can now be replaced by step 355, where for every iteration, the equiprobable realization of the pair $(p_c; \rho)_i$ is generated. Once the value for $T_{2oc}$ is obtained at step 360, an estimate for the pore geometric factor v can be calculated according to Eq. 11 at step 375.

After N iterations, the conditional probability density function for v can be generated at step 385. Hence, a station measurement of permeability may be used to infer a conditional v distribution, thus allowing the generation of the $S_{cr}$ distribution throughout a stratigraphic layer. Then a continuous log of $S_{cr}$ may be generated. It will be appreciated that a bivariate probability density function for $(p_c,v)$ can also be generated from this embodiment and used in the embodiment of FIG. 1 in lieu of the $(p_c,v)$ samples generated at step 150.

Figure 4:
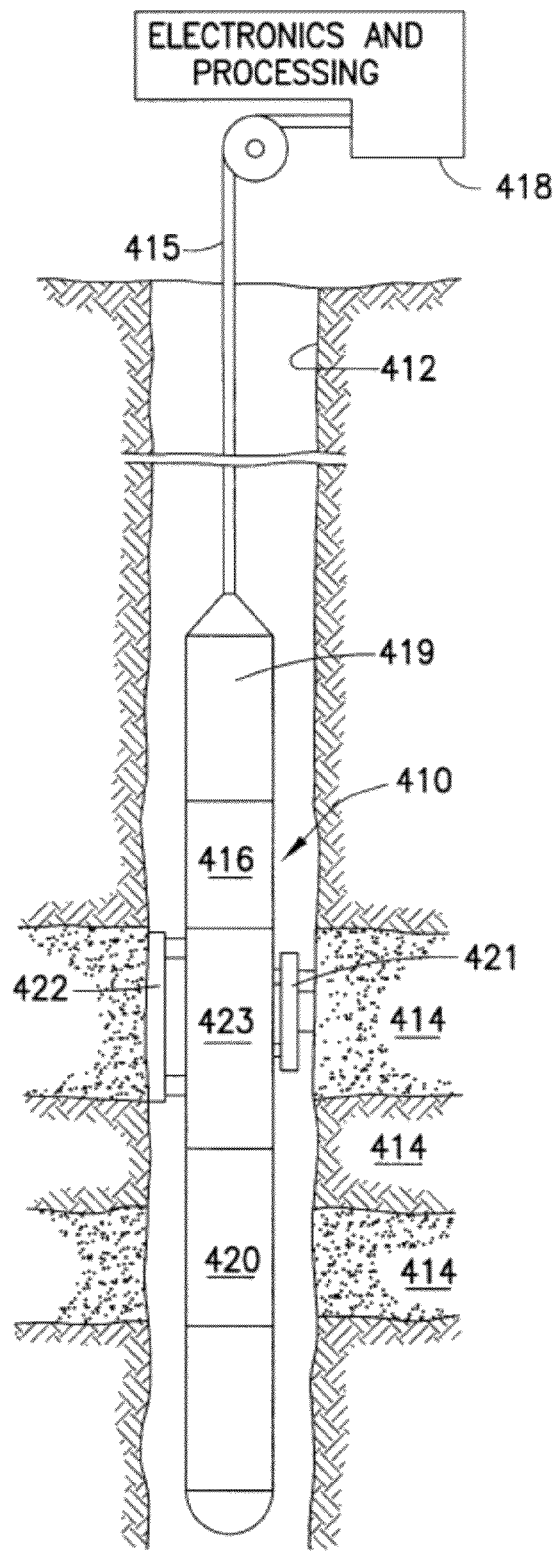
FIG. 4 is a schematic diagram of a borehole tool in a formation and a system for generating logs of residual carbon dioxide saturation in the formation utilizing any of the methods of FIGS. 1 through 3.

A logging apparatus for carrying out the previously-described methods is shown schematically in FIG. 4. More particularly, a tool 410 is shown suspended in a borehole 412 traversing a formation 414 from the lower end of a typical multiconductor cable 415 that is spooled in a usual fashion on a suitable winch (not shown) on the formation surface. On the surface, the cable 415 is preferably electrically coupled to an electrical control/processor system 418. The tool includes an elongated body 419 which encloses the downhole portion of the tool control system 416. The elongated body 419 includes an NMR assembly or module 420 (such as a CMR or a CMR-Plus type tool or MR-Scanner) typically including magnets (not shown), an antenna (not shown) and electronics (not shown). The tool also optionally carries an MDT-type module 423 including a selectively extendable fluid admitting assembly 421 (where injection or drawdown is desired), a selectively extendable tool anchoring member 422 which may be arranged on an opposite side of the body from the fluid admitting assembly, and a fluid analysis module (not shown) through which the obtained fluid flows. With the provided tool, the electronics 418 on the surface (e.g. properly programmed computer/processor apparatus) may be used to control the tool 410 such that NMR measurements are obtained and processed or pre-processed downhole and forwarded to the surface for further processing based on the previously described methods. The results of the processing by the uphole processing system 418 are preferably one or more logs of residual carbon dioxide saturation as a function of formation depth.

One example of an output of processing system 418 is seen in a fabricated FIG. 5a where the residual carbon dioxide saturation determination (estimation) is shown as a function of formation depth, i.e., as a log. The log may be provided on paper or may be displayed on a monitor or screen. The residual carbon dioxide saturation log may be used as an input into the reservoir model to predict performance of the storage site including predictions for $CO_2$ plume migration during and after injection, and uncertainty analysis in the performance of the storage site, as disclosed in U.S. Ser. No. 12/768, 021 to Chugunov N. V. et al, entitled "Method for Uncertainty Quantification in the Performance and Risk Assessment of a Carbon Dioxide Storage Site", which is hereby incorporated by reference herein in its entirety.

Another example of an output of processing system 418 is seen in a fabricated FIG. 5b where the residual carbon dioxide saturation determination (estimation) is shown as a probability density function (pdf) as a function of formation depth. The pdf may be shown in different manners, e.g., by color or intensity. Thus, as seen in FIG. 5b, a gray scale is used to show the likelihoods of the $S_{cr}$ value at different locations in the formation. While the log of FIG. 5b is not shown to be smooth, it will be appreciated by those skilled in the art that depending upon the granularity of the data and depending upon the use of smoothing filters, estimations, etc., FIG. 5b could be modified so that the percentile probabilities would be smooth from one depth to another along the formation. It will be appreciated that the log of FIG. 5b could be used for the same purposes as the log of FIG. 5a.

There have been described and illustrated methods and apparatus for determining residual carbon dioxide saturation in a formation utilizing NMR measurements. While particular embodiments of the invention have been described, it is not intended that the invention be limited thereto, as it is intended that the invention be as broad in scope as the art will allow and that the specification be read likewise. Thus, while particular tools have been described for obtaining nuclear magnetic resonance measurements as well as indications of formation characteristics such as permeability, it will be appreciated that other tools may be utilized provided they function to obtain equivalent measurements. In addition, while particular equations have been described as establishing relationships between certain measurements and formation properties, it will be understood that other similar equations could be utilized. Also, while certain values and/or ranges were described for certain variables of the equations, and certain techniques for selecting samples of those values were described it will be recognized that other suitable values and ranges can be used and other techniques for generating sample values utilized. It will therefore be appreciated by those skilled in the art that yet other modifications could be made to the provided invention without deviating from its spirit and scope as claimed.

What is claimed is:

1. A method of making residual carbon dioxide saturation estimates for a formation, comprising:
    a) making NMR measurements at a depth in the formation to obtain a determination of transverse magnetization decay M(t) at that depth;
    b) from M(t), determining a relaxation distribution;
    c) utilizing the relaxation distribution to determine a critical relaxation time $T_{2oc}$;
    d) utilizing $T_{2oc}$ to determine an estimate of the residual carbon dioxide saturation $S_{cr}$ at the depth in the formation; and
    e) displaying an indication of said estimate of the residual carbon dioxide saturation.

2. A method according to claim 1, wherein:
    said relaxation distribution is a clay-corrected relaxation distribution.

3. A method according to claim 2, further comprising:
    f) determining a plurality of critical relaxation times for the depth and determining a plurality of estimates of the residual carbon dioxide saturation.

4. A method according to claim 3, further comprising:
    g) generating at least one of a probability density function (pdf), a mode value, a mean value, and a value range for said residual carbon dioxide saturation from said plurality of estimates, wherein said displaying an indication comprises displaying said one of said pdf, mode value, mean value and value range.

5. A method according to claim 4, further comprising:
    h) repeating steps a)-g) at a plurality of depths in said formation wherein said displaying an indication comprises displaying a log of indications as a function of depth in said formation.

6. A method according to claim 4, wherein:
    said plurality of estimates comprises at least 100 estimates, and said different pairs of values comprises at least one 100 pairs of different pairs of values.

7. A method according to claim 5, wherein:
    said relaxation distribution is determined according to $M(t) = \phi \int_0^{T_{2b}} g_o(T_{2o}) \exp(-t/T_{2o}) dT_{2o}$, where $g_o(T_{2o})$ is said relaxation distribution, $T_{2b}$ is the bulk transverse relaxation time of fluid at said depth, and $\phi$ is porosity at said depth.

8. A method according claim 1, further comprising:
    repeating steps a)-e) at a plurality of depths in said formation wherein said displaying an indication comprises displaying a log of indications as a function of depth in said formation.

9. A method according to claim 1, wherein:
    said estimate of $S_{cr}$ is obtained according to $S_{cr} \approx \int_{T_{2oc}}^{T_{2b}} g_o(T_{2o}) dT_{2o}$.

10. A method according to 9, further comprising:
    obtaining an indication of permeability k for the formation at said depth, wherein said critical relaxation time $T_{2oc}$ is calculated according to $$T_{2oc} = \frac{2\sqrt{2k}}{\phi \rho T_{2b} + 2\sqrt{2k}} T_{2b}$$

where $\rho$ is the surface relaxivity at that depth.

11. A method according to claim 1, wherein:
    said critical relaxation time $T_{2oc}$ is determined according to $$p_c = \frac{\int_{T_{2oc}}^{T_{2b}} T_{2o}^{-v}(T_{2b} - T_{2o})^v g_o(T_{2o}) dT_{2o}}{\int_{T_0}^{T_{2b}} T_{2o}^{-v}(T_{2b} - T_{2o})^v g_o(T_{2o}) dT_{2o}}$$

where $p_c$ is the critical percolation probability and v is a pore geometry factor for the formation at that depth.

12. A method according to claim 11, wherein:
    said plurality of critical relaxation times are determined by utilizing a plurality of different pairs of values for $p_c$ and v.

13. A method according to claim 12, wherein:
    said utilizing a plurality of different pairs of values for $p_c$ and v comprises assuming probability density functions for $p_c$ and v, and selecting pairs randomly from said probability density functions.

14. A method according to claim 12, wherein:
    said utilizing a plurality of different pairs of values for $p_c$ and v comprises assuming a probability density function for $p_c$, and finding a value for v based on $p_c$ and based on a determination of a value of $T_{2wc}$ where $T_{2wc}$ is a critical spin-spin relaxation time of a wetting phase of the formation at said depth.

15. A method according to claim 14, further comprising:
    obtaining an estimate for the residual water saturation $S_{wr}$ of the formation at said depth; and
    using said estimate for the residual water saturation, determining said value of $T_{2wc}$ according to $S_{wr} = \int_0^{T_{2wc}} g_o(T_{2o}) dT_{2o}$.

16. A system for making residual carbon dioxide saturation estimates for a formation traversed by a borehole, comprising:
    a) a nuclear magnetic resonance tool capable of traversing said borehole and making nuclear magnetic resonance measurements at a depth in the formation to obtain a determination of transverse magnetization decay M(t) at that depth;
    b) a processor coupled to said nuclear magnetic resonance tool, said processor,
        1) determining a relaxation distribution from said M(t),
        2) utilizing the relaxation distribution to determine a critical relaxation time $T_{2oc}$,
        3) utilizing $T_{2oc}$ to determine an estimate of the residual carbon dioxide saturation $S_{cr}$, at the depth in the formation; and
    c) a display that displays an indication of said estimate of the residual carbon dioxide saturation.

17. A system according to claim 16, wherein:
    said relaxation distribution is a clay-corrected relaxation distribution, and said processor further determines a plurality of critical relaxation times for the depth and determines a plurality of estimates of the residual carbon dioxide saturation.

18. A system according to claim 17, wherein:
    said display shows at least one of a probability density function (pdf), a mode value, a mean value, and a value range for said residual carbon dioxide saturation from said plurality of estimates.

19. A system according to claim 18, wherein:
said display shows said at least one of a probability density function (pdf), a mode value, a mean value, and a value range for said residual carbon dioxide saturation as a function of depth in said formation.

20. A system according to claim 19, wherein:
said processor determines said relaxation distribution according to $M(t) = \phi \int_0^{T_{2b}} g(T_{2o}) \exp(-t/T_{2o}) dT_{2o}$, where $g_o(T_{2o})$ is said relaxation distribution, $T_{2b}$ is the bulk transverse relaxation time of fluid at said depth, and $\phi$ is porosity at said depth, and said estimate of $S_{cr}$ according to one of $S_{cr} \approx \int_{T_{2oc}}^{T_{2b}} g_o(T_{2o}) dT_{2o}$ and $S_{cr} \approx \int_{T_{2oc}}^{T_{2b}} g_c(T_{2o}) dT_{2o}$, where $g_c(T_{2o})$ is said clay-corrected relaxation distribution.

* * * * *